US012178539B2

(12) United States Patent
Marvi et al.

(10) Patent No.: US 12,178,539 B2
(45) Date of Patent: Dec. 31, 2024

(54) MAGNETIC NEEDLE STEERING SYSTEMS AND METHODS

(71) Applicant: Arizona Board of Regents on behalf of Arizona State University, Scottsdale, AZ (US)

(72) Inventors: Hamidreza Marvi, Chandler, AZ (US); Mahdi Ilami, Tempe, AZ (US); Reza Ahmed, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 676 days.

(21) Appl. No.: 17/435,348

(22) PCT Filed: Mar. 23, 2020

(86) PCT No.: PCT/US2020/024225
§ 371 (c)(1),
(2) Date: Aug. 31, 2021

(87) PCT Pub. No.: WO2020/191399
PCT Pub. Date: Sep. 24, 2020

(65) Prior Publication Data
US 2022/0175481 A1 Jun. 9, 2022

Related U.S. Application Data

(60) Provisional application No. 62/821,846, filed on Mar. 21, 2019.

(51) Int. Cl.
*A61B 34/00* (2016.01)
*A61B 17/00* (2006.01)
(Continued)

(52) U.S. Cl.
CPC .......... *A61B 34/73* (2016.02); *A61B 17/3403* (2013.01); *A61B 1/00158* (2013.01);
(Continued)

(58) Field of Classification Search
CPC .............. A61B 34/73; A61B 2034/731; A61B 2034/732; A61B 2034/733;
(Continued)

(56) References Cited

U.S. PATENT DOCUMENTS 6,834,201 B2  12/2004  Gillies et al.
7,873,402 B2  1/2011  Shachar
(Continued)

OTHER PUBLICATIONS

Abolhassani, N. et al., "Needle insertion into soft tissue: A survey," Medical Engineering & Physics, vol. 29, Issue 4, May 2007, Elsevier, pp. 413-431.
(Continued)

*Primary Examiner* — Chao Sheng
(74) *Attorney, Agent, or Firm* — Withrow & Terranova, P.L.L.C.; Vincent K. Gustafson

(57) ABSTRACT

A steerable assembly comprises an elongated body structure with an implement arranged at a distal end thereof, wherein a premagnetized material is arranged closer to the distal end than a proximal end, and is configured to enable steering of the implement through tissue of an animal body responsive to application of a magnetic field eternal to the body. A method for guiding passage of an implement through tissue includes altering strength and/or position of at least one magnetic field source external to an animal body to interact with and effectuate movement of a premagnetized material inserted into the animal body.

11 Claims, 11 Drawing Sheets

(51) Int. Cl.
A61B 17/34 (2006.01)
A61B 1/00 (2006.01)
A61B 90/00 (2016.01)
A61M 25/01 (2006.01)
(52) U.S. Cl.
CPC .............. A61B 2017/00876 (2013.01); A61B 2090/374 (2016.02); A61M 25/0127 (2013.01)
(58) Field of Classification Search
CPC .......... A61B 17/3403; A61B 2090/374; A61B 1/00158; A61B 2017/00876; A61M 25/0127
See application file for complete search history.

(56) References Cited

U.S. PATENT DOCUMENTS

| | | | |
|---|---|---|---|
| 8,088,129 | B2 | 1/2012 | Werp et al. |
| 9,770,238 | B2 | 9/2017 | Bonutti |
| 2008/0027313 | A1* | 1/2008 | Shachar ................. A61B 5/064 600/424 |
| 2010/0063384 | A1 | 3/2010 | Kornblau et al. |
| 2016/0331358 | A1 | 11/2016 | Gordon |
| 2018/0000466 | A1 | 1/2018 | Park et al. |
| 2018/0185090 | A1* | 7/2018 | Coates ..................... G01R 5/26 |
| 2019/0008557 | A1 | 1/2019 | Lenker et al. |

OTHER PUBLICATIONS

Adebar, T. et al., "Methods for Improving the Curvature of Steerable Needles in Biological Tissue," IEEE Transactions on Biomedical Engineering, vol. 63, Issue 6, Jun. 2016, IEEE, 11 pages.
Alterovitz, R. et al., "Planning for Steerable Bevel-tip Needle Insertion Through 2D Soft Tissue with Obstacles," Proceedings of the 2005 IEEE International Conference on Robotics and Automation, Apr. 18-22, 2005, Barcelona, Spain, IEEE, 7 pages.
Bernardes, M. et al., "Semi-automatic needle steering system with robotic manipulator," Proceedings of the IEEE International Conference on Robotics and Automation, May 2012, IEEE, 7 pages.
Bigot, A. et al., "Magnetic Resonance Navigation of a Bead Inside a Three-Bifurcation PMMA Phantom Using an Imaging Gradient Coil Insert," IEEE Transactions on Robotics, vol. 30, No. 3, Feb. 2014, IEEE, pp. 719-727.
Burrows, C. et al., "Experimental characterisation of a biologically inspired 3D steering needle," 2013 13th International Conference on Control, Automation and Systems (ICCAS 2013), Oct. 20-23, 2013, Gwamgju, South Korea, IEEE, 6 pages.
Cabreros, S. et al., "Remote Electromagnetic Vibration of Steerable Needles for Imaging in Power Doppler Ultrasound," IEEE International Conference on Robotics and Automation, May 2015, IEEE, pp. 2244-2249.
Dencker, D. et al., "Image Fusion and Electromagnetic Needle Tracking for the Biopsy of Pelvic Lesions—Report of 2 Cases," Ultrasound International Open, vol. 1, No. 1, Jul. 2015, 2 pages.
Dong, W. et al., "The tip interface mechanics modeling of a bevel-tip flexible needle insertion," 2012 IEEE International Conference on Mechatronics and Automation, Aug. 5-8, 2012, Chengdu, China, IEEE, 6 pages.
Gilbert, H. et al., "Concentric Tube Robots as Steerable Needles: Achieving Follow-the-Leader Deployment," IEEE Transactions on Robotics, vol. 31, Issue 2, Feb. 10, 2015, IEEE, 14 pages.
Glozman, D. et al., "Flexible Needle Steering and Optimal Trajectory Planning for Percutaneous Therapies," Proceedings of the 7th International Conference on Medical Image Computing and Computer-Assisted Intervention (MICCAI 2004), Lecture Notes in Computer Science 3217, Sep. 2004, Saint-Malo, France, Springer-Verlag Berlin Heidelberg, pp. 137-144.
Jahya, A. et al., "Observations of three-dimensional needle deflection during insertion into soft tissue," 2012 4th IEEE RAS EMBS International Conference on Biomedical Robotics and Biomechatronics (BioRob), Jun. 24-27, 2012, Rome, Italy, IEEE, 6 pages.
Khadem, M. et al., "Robotic-Assisted Needle Steering Around Anatomical Obstacles Using Notched Steerable Needles," IEEE Journal of Biomedical and Health Informatics, vol. 22, No. 6, Dec. 6, 2017, IEEE, 12 bages.
Kummer, M.P. et al."OctoMag: An Electromagnetic System for 5-DOF Wireless Micromanipulation," IEEE Transactions on Robotics, vol. 26, Issue 6, Oct. 7, 2010, IEEE, pp. 1006-1017.
Majewicz, A. et al., "Evaluation of robotic needle steering in ex vivo tissue," 2010 IEEE International Conference on Robotics and Automation, May 3-7, 2010, Anchorage, AK, USA, IEEE, 6 pages.
Martel, S. et al., "Automatic navigation of an untethered device in the artery of a living animal using a conventional clinical magnetic resonance imaging system," Applied Physics Letters, vol. 90, Issue 11, Mar. 14, 2007, AIP Publishing, 3 pages.
Narayan, M. et al., "Data-Driven Detection of Needle Buckling Events in Robotic Needle Steering," Journal of Medical Robotics Research, vol. 3, No. 3, Mar. 2018, 13 pages.
Okazawa, S. et al., "Hand-held steerable needle device," IEEE/ASME Transactions on Mechatronics, vol. 10, Issue 3, Jun. 2005, IEEE, pp. 285-296.
Reed, K. et al., "Robot-Assisted Needle Steering," IEEE Robotics & Automation Magazine, vol. 18, Issue 4, Dec. 2011, IEEE, 12 pages.
Reed, K. et al., "Controlling a robotically steered needle in the presence of torsional friction," IEEE International Conference on Robotics and Automation, May 12-17, 2009, Kobe, Japan, IEEE, 6 pages.
Reed, K. et al., "Modeling and Control of Needles with Torsional Friction," IEEE Transactions on Biomedical Engineering, Dec. 2009, vol. 56, No. 12, 36 pages.
Secoli, R. et al., "Closed-loop 3D motion modeling and control of a steerable needle for soft tissue surgery," IEEE International Conference on Robotics and Automation, May 6-10, 2013, Karlsruhe, Germany, IEEE, 6 pages.
Sitzman, B.T. et al., "The Effects of Needle Type, Gauge, and Tip bend on Spinal Needle Deflection," Anesthesia & Analgesia, vol. 82, No. 2, Feb. 1996, International Anesthesia Research Society, pp. 297-301.
Swaney, P.J. et al., "A Flexure-Based Steerable Needle: High Curvature With Reduced Tissue Damage," IEEE Transactions on Biomedical Engineering, vol. 60, No. 4, Nov. 27, 2012, IEEE, 4 pages.
Swensen, J.P. et al., "Torsional Dynamics Compensation Enhances Robotic Control of Tip-Steerable Needles," IEEE International Conference on Robotics and Automation, May 14-18, 2012, Saint Paul, MN, USA, IEEE, 6 pages.
Swensen, J.P. et al., "Torsional Dynamics of Steerable Needles: Modeling and Fluoroscopic Guidance," IEEE Transactions on Biomedical Engineering, vol. 61, No. 11, May 21, 2014, IEEE, 11 pages.
Torabi, M. et al., "Guiding medical needles using single-point tissue manipulation," IEEE International Conference on Robotics and Automation, May 12-17, 2009, Kobe, Japan, IEEE, 6 pages.
Van De Berg, N. et al., "Design Choices in Needle Steering—A Review," IEEE/ASME Transactions on Mechatronics, vol. 20, Issue 5, Oct. 2015, IEEE, pp. 2172-2183.
Van De Berg, N. et al., "Design of an actively controlled steerable needle with tendon actuation and FBG-based shape sensing," Medical Engineering & Physics, vol. 37, No. 6, Jun. 2015, Elsevier Ltd., pp. 617-622.
Van De Berg, N. et al., "The influence of tip shape on bending force during needle insertion," Scientific Reports, vol. 7, No. 1, Jan. 11, 2017, 8 pages.
Wang, Y.Z. et al., "Towards a Magnetic Articulated Needle," Advanced Materials Research, vols. 393-395, Nov. 2011, pp. 1060-1063.
Webster, R.J. et al., "Design Considerations for Robotic Needle Steering," Proceedings of the 2005 IEEE International Conference on Robotics and Automation, Apr. 18-22, 2005, Barcelona, Spain, IEEE, 7 pages.

(56) References Cited

OTHER PUBLICATIONS

Wedlick et al., "Characterization of Pre-Curved Needles for Steering in Tissue," IEEE 2009 Annual International Conference of the IEEE Engineering in Medicine and Biology Society, Sep. 2009, Minneapolis, MN, IEEE, 4 pages.
International Search Report and Written Opinion for International Patent Application No. PCT/US2020/024225, mailed Jun. 26, 2020, 17 pages.

* cited by examiner

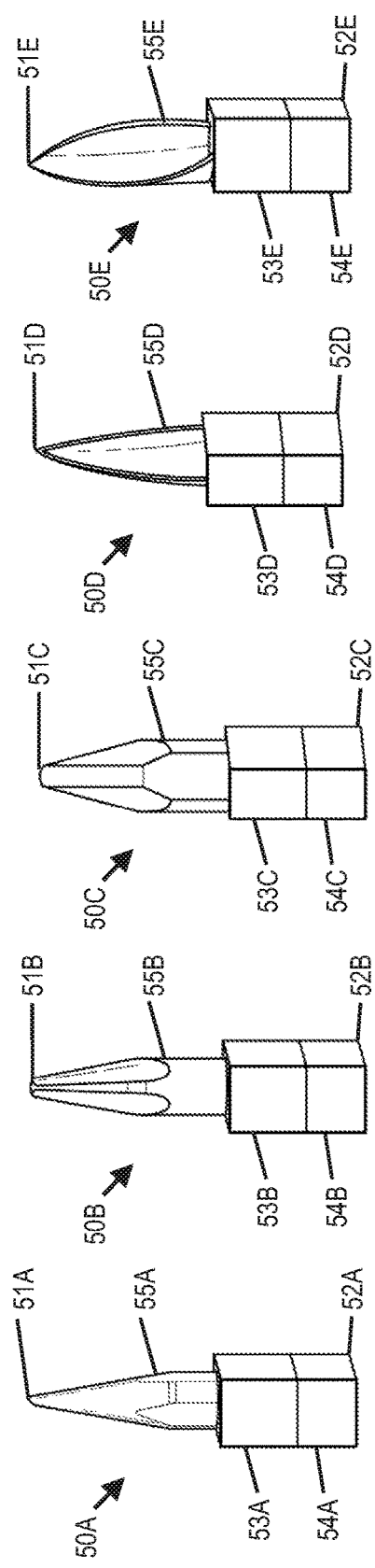
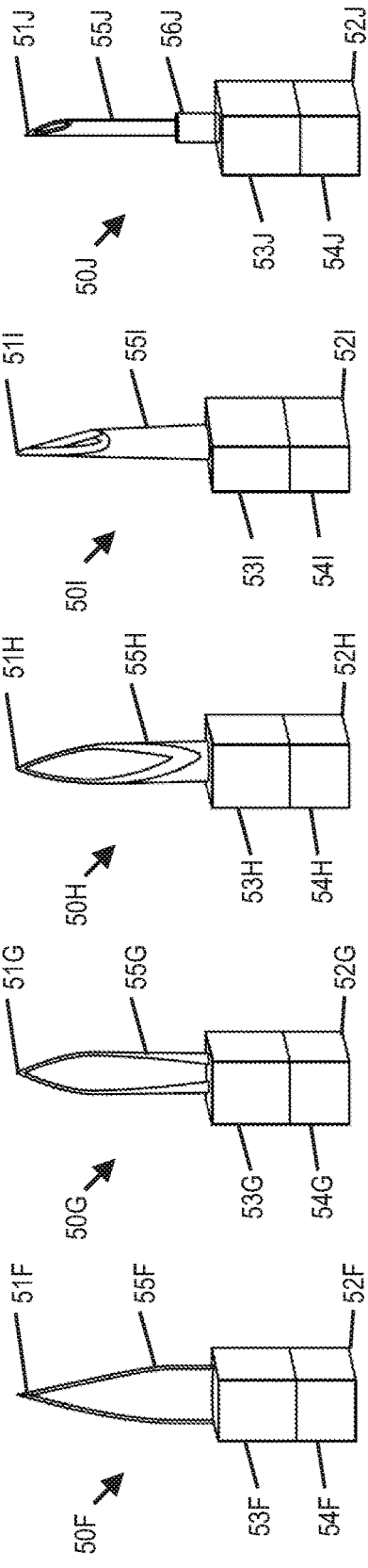
FIG. 3A  FIG. 3B  FIG. 3C  FIG. 3D  FIG. 3E
FIG. 3F  FIG. 3G  FIG. 3H  FIG. 3I  FIG. 3J

| Case | Transition Type | Desired AoA | Max. Deviation of the Mean from the Path | RMS of the error |
|---|---|---|---|---|
| 1 | Soft to Stiff | 90 Degrees | 0.8 mm | 0.6 mm |
| 2 | Soft to Stiff | 45 Degrees | 2.3 mm | 0.8 mm |
| 3 | Soft to Stiff | 22.5 Degrees | 0.5 mm | 0.7 mm |
| 4 | Stiff to Soft | 90 Degrees | 0.8 mm | 0.5 mm |
| 5 | Stiff to Soft | 45 Degrees | 0.8 mm | 1.4 mm |
| 6 | Stiff to Soft | 22.5 Degrees | 1.0 mm | 2.1 mm |

*FIG. 9*

| Phantom Tissue Material | Radius of Curvature | Max. Deviation of the Mean from the Path | RMS of the error |
|---|---|---|---|
| Soft | 10.2 mm | 0.8 mm | 1.3 mm |
| Soft | 20.3 mm | 0.7 mm | 1.3 mm |
| Soft | 30.5 mm | 0.6 mm | 1.2 mm |
| Stiff | 10.2 mm | 0.8 mm | 1.4 mm |
| Stiff | 20.3 mm | 1.2 mm | 1.5 mm |
| Stiff | 30.5 mm | 1.5 mm | 1.7 mm |

*FIG. 10*

MAGNETIC NEEDLE STEERING SYSTEMS AND METHODS

CROSS-REFERENCE TO RELATED APPLICATIONS

This application is a 35 U.S.C. § 371 national phase filing of International Application No. PCT/US2020/024225 filed on Mar. 23, 2020, and claims benefit of U.S. Provisional Patent Application No. 62/821,846 filed on Mar. 21, 2019, wherein the entire contents of the foregoing applications are hereby incorporated by reference herein.

BACKGROUND

Needles are among the least invasive surgical tools available to doctors and surgeons. The wound caused by a needle is easily and quickly repaired by the body and is, therefore, the preferred method of administering liquids to, or drawing liquids from, the body.

Surgical needles are commonly used in percutaneous diagnostic and therapeutic procedures. These procedures include tissue sample removal (biopsy), internal radiotherapy (brachytherapy), thermal ablations, and targeted drug delivery. The success of these procedures highly depends on the accuracy of needle placement at target locations. Various surgical procedures utilize needles connected to tubular bodies that are inserted into patients (e.g., for intravascular use), with such tubular bodies being embodied in catheters, cannulas, guide wires, or the like.

Inflexible needles can only reach a target just under the skin, with such a target not being protected by bone or sensitive tissues. However, needles with flexible long shafts can be steered around sensitive or protective internal obstacles. In traditional needle steering techniques, such needles are steered by the imbalance of forces acting on the tip of a beveled needle during insertion.

Needle steering has been achieved in various ways, but conventional techniques utilize the same basic concept—namely, exploiting asymmetric forces on an asymmetric needle tip during insertion. As the needle tip is pushed forward, it also moves slightly sideways, motivated by the radial component of the force acting on the tip. The magnitude of this sideways movement depends on the tip geometry, needle stiffness, tissue stiffness, bevel angle, and other properties of the needle-tissue interactions. The needle (or an associated tubular structure connected to the needle) is rotated at the base to control the orientation of the tip, thus rotating the direction of the asymmetric force and permitting the trajectory of the needle tip to be controlled. An asymmetric needle tip may be beveled, complex, active, inactive, programmable, composite, or articulated.

Advances in needle steering techniques have typically focused on innovation of the mechanical needle design and the mode by which a needle may be manipulated. Past needle steering techniques have been classified into two sub-groups: passive and active. Base manipulation, rotated-beveled needle, pre-curved needle tip, pre-bent needle tip, notched shaft, and other techniques employing passive needle modifications fall within the passive category. Passive bevel-tip needles utilize unbalanced forces on a needle tip to create a curved path inside the tissue and reach the target. This curved path could be used to maneuver around sensitive organs during surgical intervention. However, trajectory planning with passive needles is complicated and sometimes inaccurate. Rotation of a needle while the needle advances through tissue is not only difficult, but also increases the risk of tissue damage. Conventional pre-curved needles have been used by others to achieve a minimal radius of curvature of about 15.5 mm. A radius of curvature of 47.1 mm has been achieved using a conventional pre-bent needle tip. A conventional notched needle tip has been used to achieve a minimum radius of curvature of 171 mm.

In contrast to passive needles, active needles can at least partially compensate for possible misalignments via their actuation forces. Organ movements, physiological processes such as breathing, and human errors, are typical causes for these misalignments. Active needle steering techniques include telescoping cannula, programmable bevel, tissue manipulation, and controlled articulating tip. These methods utilize an additional level of control beyond asymmetric forces, whereby one or more properties of a needle shaft or tip, or needle/tissue interactions, can be manipulated via some extra means. With the help of the active needle's actuation and control, surgeons can guide a needle through a desired trajectory with increased accuracy. A complex needle having four independently actuated interlocked shafts that could be extended or retracted to alter the tip geometry has been used to achieve a radius of curvature as small as 58 mm. A conventional needle having four actuation cables running alongside the shaft and connected to the tip has been used to alter the tip angle while achieving a radius of curvature of 181 mm. Use of an actuated hinge near the needle tip has produced turning radii under 5 cm.

Electromagnetic sensing and actuation have also been used for active needle steering. Magnetic actuation has been used to vibrate small permanent magnets inside a needle shaft, to produce vibrations for ultrasound needle tracking. Electromagnetic needle tracking employing a magnetic sensor inside a needle tip has been used. A needle with a magnetic head has been used with magnetic fields to orient the head, in combination with application of mechanical force at the base of the needle for insertion and advancement.

Conventional needle manipulation relies upon pushing and rotating the base of a long shaft to effectuate movement of a needle at a distal end of the shaft. The conventional method introduces some inherent challenges: compression and torsion effects in the shaft, tissue damage during tip rotations, and restricted reachable work space due to the limited radius of curvature.

Buckling of a needle shaft is one challenge associated with conventional needle steering methods. In conventional needle steering, there is a possibility of the shaft slicing through tissue during lateral movements, which could arise in a buckling event. When a needle shaft buckles, whether it be at a point inside or outside the tissue, unpredictable movements of the needle can damage the tissue. In the conventional needle steering method, flexible needles need to be supported at the base to prevent buckling in the needle shaft at the entry point as it penetrates the tissue. Too much force exerted on the needle shaft during deep insertions can cause the needle shaft to slice through the tissue laterally, with or without buckling. Modeling has been used to detect buckling events that occur when a needle tip encounters a rigid object it cannot penetrate, demonstrating that buckling can occur due to collisions and inhomogeneity in the tissue. Buckling is a concern to the conventional needle steering method only because the needle is actuated by a compression force acting along the shaft. Indeed, the fact that the shaft must be able to withstand significant compression stress conflicts with the necessity that the shaft also must be flexible enough to permit steering. This conflict is an inherent limitation to convention needle steering methods.

Another challenge associated with conventional needle steering methods is addressing torsion in a needle shaft. In the conventional method of needle steering, the needle is rotated at the base to produce a rotation at the tip to steer the needle. One inherent drawback to this control method is that there are complex torsional effects along the shaft that cause the base and tip to rotate out of sync. Conventionally, the discrepancy between the base and tip rotations can be as high as 45 degrees for a needle insertion of only 10 cm. Although several approaches have improved the performance of the conventional needle steering method through modelling and controlled compensation of these torsional effects, these effects can lead to poor performance in methods that do not compensate for torsion effects in the shaft.

Rotational tissue damage is another concern associated with conventional needle steering methods. To obtain radii of curvature greater than the natural curvature for a particular needle/tissue pair using conventional needle steering methods, the rotation of a needle must be duty cycled to redirect the asymmetric forces at the tip during insertion. This method of using repeated rotational patterns to control the asymmetrical forces on the needle tip is called duty-cycling. For pre-bent, pre-curved, and some complex needle designs, duty cycled rotation of the needle tip can cause significant additional tissue damage during insertion.

Yet another challenge associated with conventional needle steering methods is restricted reachable workspace within tissue. Because of the aforementioned conflict between stiffness and flexibility of the needle shaft, the achievable radius of curvature has heretofore been restrictively large, thereby limiting the reachable region of the needle tip. The reachable region in needle steering is a cone with a curved slope similar in shape to a concave paraboloid, but such that the curve of the sloped face is defined by the minimal radius of curvature for the particular needle/tissue pairing.

The smallest radii of curvature found in the literature by the inventors as of March 2019 was 15.5 mm for a 0.48 mm diameter superelastic nitinol wire with a 15 mm pre-curve, extending 90 degrees in an arc about its center of bending. A more reliable and controllable radius of curvature is taken to be 31 mm, for the same needle and prebend radius with a 40 degree arc. Needles with more than a 40 degree arc and 15 mm radius have been reported to lose their ability to be steadily rotated, and instead store energy until they snap (i.e., spring-like) into a new configuration. Furthermore, it has been reported that needles having this level of pre-curve experience significant rotational resistance and rotation discrepancy between the base and tip. These behaviors are not desirable for steering needles within tissue.

Summarizing limitations associated with the art, needle steering has not achieved widespread clinical use due to several limitations, including: (1) buckling and compression effects in the shaft and needle rotation cause excessive tissue damage; (2) torsion effects on the shaft and needle deflection at tissue boundaries lead to control difficulties; and (3) restricted radius of curvature results in limited workspace. Magnetically steered catheters and continuum manipulators also suffer from limited curvature and the possibility of buckling.

In view of the foregoing, the art continues to seek improvement in systems and methods for controlling operation of steerable surgical devices, including devices comprising needles, to enhance their utility.

SUMMARY

The present disclosure relates to steerable assemblies that enable steering of an implement through or within tissue of an animal body responsive to application of a magnetic field external to the animal body, and associated methods for guiding passage of an implement through or within tissue of an animal body. Such method includes altering strength and/or position of at least one magnetic field source external to an animal body to interact with a premagnetized material inserted into the animal body to effectuate movement of the implement within the animal body. As used herein, the term "animal body" is intended to encompass a body of a human or non-human animal.

In one aspect, the disclosure relates to a steerable assembly comprising: an elongated body structure having a proximal end and a distal end; and an implement arranged at a distal end of the elongated body structure; wherein a premagnetized material is arranged closer to the distal end than the proximal end, and the premagnetized material is configured to enable steering of the implement through or within tissue of an animal body responsive to application of a magnetic field generated by a magnetic field source that is external to the animal body.

In certain embodiments, the premagnetized material comprises a permanent magnet. In certain embodiments, the premagnetized material comprises a ferromagnetic material. In certain embodiments, the premagnetized material comprises an electromagnet. In certain embodiments, the premagnetized material comprises a paramagnetic or superparamagnetic material (e.g., $Fe_3O_4$, optionally in a microparticulate or nanoparticulate form).

In certain embodiments, at least a portion of the implement comprises the premagnetized material. In certain embodiments, the implement comprises a needle. In certain embodiments, the needle is hollow. In certain embodiments, the premagnetized material is rigidly coupled to the implement. In certain embodiments, the implement comprises a surgical tool. In certain embodiments, the implement comprises at least one of a camera or an optical fiber.

In certain embodiments, the elongated body structure comprises a flexible and/or elastic material. In certain embodiments, the elongated body structure comprises a hollow tube. In certain embodiments, the elongated body structure comprises a catheter. In certain embodiments, the elongated body structure comprises an electrical conductor. In certain embodiments, the elongated body structure comprises an optical fiber.

In certain embodiments, a center of mass of the premagnetized material is located less than 5 cm, or less than 2 cm, or less than 1 cm, from the distal end of the elongated body structure.

Another aspect of the disclosure relates to a system comprising a steerable assembly as disclosed herein, and at least one magnetic field source configured to interact with the premagnetized material to effect movement of the implement through or within tissue of the animal body when the implement is arranged within the animal body, wherein the at least one magnetic field source is external to the animal body. In certain embodiments, the at least one magnetic field source comprises a plurality of magnetic field sources. In certain embodiments, the at least one magnetic field source comprises a magnetic resonance imaging apparatus.

Yet another aspect of the disclosure relates to a system comprising: at least one magnetic field source; and a steerable assembly that comprises an elongated body structure, an implement arranged at a distal end of the elongated body structure, and a premagnetized material arranged closer to the distal end than to a proximal end of the elongated body structure; wherein the at least one magnetic field source is configured to interact with the premagnetized material to effect movement of the implement within an animal body when the implement is arranged within the animal body.

In certain embodiments, the at least one magnetic field source comprises at least one magnetic coil. In certain embodiments, the at least one magnetic field source comprises a magnetic resonance imaging system. In certain embodiments, the at least one magnetic field source comprises at least one permanent magnet. In certain embodiments, the at least one magnetic field source comprises a plurality of magnetic field sources. Using a permanent magnet or a bigger electromagnetic system enables a larger workspace and/or stronger magnetic fields for steering a magnetic needle in stiffer tissues.

Another aspect of the disclosure relates to a method for guiding passage of an implement through or within tissue of an animal body, the method comprising: inserting at least a portion of a steerable assembly into the animal body, the steerable assembly comprising an elongated body structure, an implement arranged at a distal end of the elongated body structure, and a premagnetized material arranged closer to the distal end than to a proximal end of the elongated body structure; providing at least one magnetic field source external to an animal body; and altering at least one of strength or position of the at least one magnetic field source to interact with the premagnetized material to effectuate movement of the implement within the animal body.

In certain embodiments, the at least one magnetic field source comprises a plurality of magnetic field sources. In certain embodiments, the altering of at least one of strength or position of the at least one magnetic field source comprises altering strength of multiple magnetic field sources of the plurality of magnetic field sources.

In certain embodiments, movement of the implement within the animal body exerts a pulling force on the elongated body structure. In certain embodiments, movement of the implement within the animal body is performed without repeated rotation of the implement.

In certain embodiments, the at least one magnetic field source comprises at least one magnetic coil. In certain embodiments, the at least one magnetic field source comprises a magnetic resonance imaging system. In certain embodiments, the at least one magnetic field source comprises at least one permanent magnet, and wherein the altering of at least one of strength or position of the at least one magnetic field source comprises altering position of the at least one permanent magnet.

In certain embodiments, the elongated body structure comprises a fluidic passage, and the method comprises delivering a therapeutic agent through the fluidic passage and the implement to the tissue. In certain embodiments, the method further comprises extracting a tissue sample from the animal body using the implement.

In certain embodiments, at least a portion of the implement comprises the premagnetized material. In certain embodiments, the premagnetized material is rigidly coupled to the implement. In certain embodiments, the implement comprises a surgical tool. In certain embodiments, the implement comprises at least one of a camera or an optical fiber. In certain embodiments, the method further comprises capturing at least one image of the tissue using the implement.

In certain embodiments, movement of the implement within the animal body caused by interaction between the premagnetized material and the at least one magnetic field source comprises advancement of the implement into the animal body away from a point of insertion of the implement into the animal body.

In another aspect, the disclosure relates to a steerable assembly comprising: an elongated body structure having a proximal end and a distal end; and an implement arranged at a distal end of the elongated body structure; wherein an electromagnet is arranged closer to the distal end than the proximal end, and the electromagnet is configured to enable steering of the implement through or within tissue of an animal body responsive to application of a magnetic field generated by a magnetic field source that is external to the animal body.

BRIEF DESCRIPTION OF DRAWINGS

FIGS. 3A-3J provide side elevational views of ten magnetic needle tips that were selected and fabricated for characterization.

FIG. 9 is a table summarizing experimental cases and the associated deviation of the experimental mean from the ideal path for passage of magnetic needle tips through interfaces between phantom tissues of different stiffnesses according to the paths characterized in FIGS. 7A-7B.

FIG. 10 is a table summarizing experimental cases and the associated maximum deviation of the experimental mean from the ideal path for passage of magnetic needle tips along circular paths through three different radii of curvature in soft and stiff phantom tissues as characterized in FIGS. 8A-8B.

DETAILED DESCRIPTION

Figure 1:
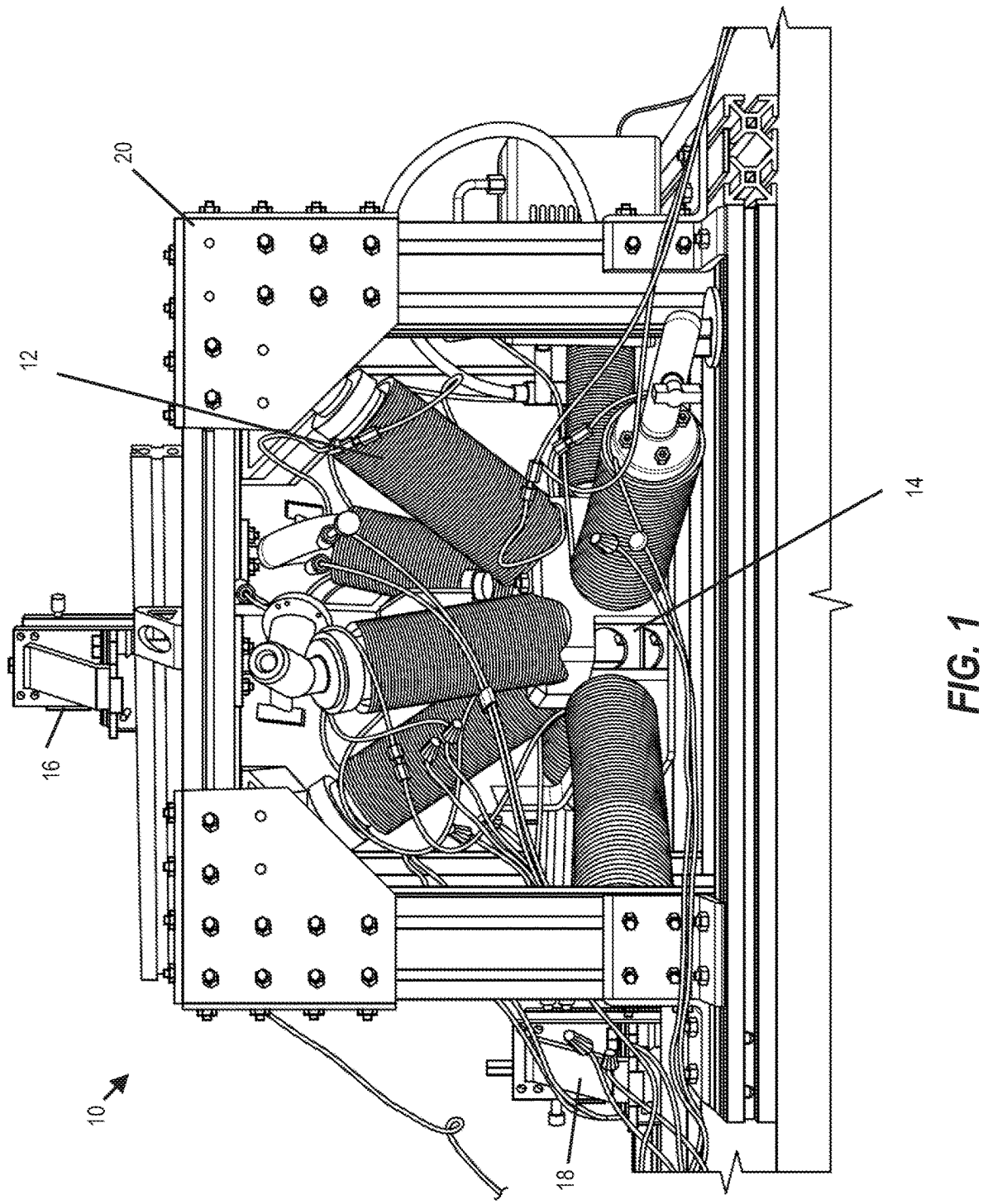
FIG. 1 is a side elevational view of a magnetic field generating system used to actuate a magnetic needle tip with associated cameras used to track the magnetic needle tip.

The present disclosure relates to steerable assemblies that enable steering of an implement through or within tissue of an animal body responsive to application of a magnetic field external to the animal body, and relates to methods for guiding passage of an implement through or within tissue of an animal body by altering strength and/or position of at least one magnetic field source external to an animal body to interact with a premagnetized material inserted into the animal body to effectuate movement of the implement within the animal body. In certain embodiments, needle steering includes magnetic manipulation of a sharp magnetic needle tip, having an elastic, non-load bearing shaft. In contrast to previous applications of electromagnetic actuation to needle steering, at least certain methods disclosed herein utilize electromagnetic fields applied by at least one magnetic field source external to tissue for both steering and for advancement of a needle into the tissue. In particular, one distinction between methods disclosed herein and conventional needle steering techniques is that external magnetic actuation force is used for pulling a needle through tissue instead of pushing and rotating the base of a long shaft to effectuate movement of a needle at a distal end of the shaft. Restated, various embodiments disclosed herein utilize electromagnetic pulling actuation instead of mechanical pushing actuation, thereby eliminating numerous issues associated with conventional needle steering, magnetically steered catheters, and continuum manipulators. At least certain methods replace a conventional long-shaft needle with an elastic shaft attached to a magnetic needle tip, and replace motorized actuation with electromagnetic actuation. This change in material and actuation method eliminates many issues associated with compression and torsion effects. Implications of the disclosed needle steering method with respect to numerous limitations encountered with conventional needle steering (compression and torsion effects in the shaft, tissue damage during tip rotations, and restricted reachable work space due to the limited radius of curvature) are discussed below.

In methods according to the present disclosure, a conventional needle shaft is replaced by an elastic shaft that is not load-bearing. Needle manipulation methods according to at least certain embodiments utilize only magnetic forces and torques to both steer and advance a sharp magnetic tip, thereby allowing arbitrarily soft shafts that are pulled rather than pushed. By pulling the needle tip through tissue using externally applied magnetic forces instead of pushing at the base of a load-bearing shaft supporting a needle, shaft buckling is no longer a concern, and the conflict between shaft stiffness and flexibility is eliminated. That is, changing the actuation method to eliminate compression stresses in the shaft will eliminate the very possibility of buckling. Eliminating buckling as a possible issue also allows for a drastic improvement in the minimum turning radius of the needle.

Magnetically actuated steering methods disclosed herein do not rely on the asymmetry of the needle tip for steering, and thus does not require torsional (rotational) control of rotation of a needle about a longitudinal axis of the needle. Since steering methods disclosed herein do not require rotation of a needle about the longitudinal axis to achieve arbitrary radii of curvature, the risk of tissue damage induced by duty-cycled tip rotation is eliminated. Moreover, tighter radius of curvature values may be obtained by magnetically actuated steering methods according to the present disclosure, thereby expanding the reachable region of a needle tip relative to a conventional steerable needle.

According to the categorization scheme previously outlined herein, the disclosed method of needle steering may be considered passive. Although it differs fundamentally from traditional needle steering techniques, it does not operate by moving parts and requires only control of a magnetic field generating system.

In certain embodiments, a magnetic needle tip (or similar implement) and associated elongated body structure may be distinguished from a catheter in that it is intended only to penetrate tissue, but is a continuum manipulator. Catheters are blunt, flexible rods generally meant to maneuver inside the existing channels in the body, to perform a host of tasks. Magnetically steered catheters and continuum manipulators use magnetic field generation systems to manipulate a device's end effector, which houses a permanent magnet or other premagnetized material.

The embodiments set forth herein represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element is referred to as being "connected" or "coupled" to another element, it can be directly connected or coupled to the other element, or intervening elements may be present. In contrast, when an element is referred to as being "directly connected" or "directly coupled" to another element, there are no intervening elements present.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Magnetic Coil System

In certain embodiments, an eight-coil electromagnetic field generation apparatus may be used to produce and manipulate the actuating magnetic field. Such an apparatus has been disclosed by Kummer, M. P., et al., Octomag: An electromagnetic system for 5-dof wireless micromanipulation. IEEE Transactions on Robotics 26:1006-1017, 2010. This apparatus enables five degrees of freedom (DOF) magnetic control of a small magnetic body in a 1.3 cubic inch workspace. The five DOF include three DOF of translation and two DOF of rotation; the rotation about the main axis of a magnet is not achievable with this system. This level of remote control is provided using an array of stationary current-controlled electromagnetic coils, with each coil is composed of a solid iron core and 712 wraps of 14-gauge copper wire in six layers. Each coil may further include an aluminum housing. Two power supplies are used; a TITAN F1208 capable of providing 60 A and up to 1200 W of electrical power, and an eFuel PSU50A V2 capable of providing 50 A and up to 1200 W of electrical power. Four Sabertooth 2×25 dual motor drivers are used as amplifiers between the power supplies and coils. Amplifiers are connected to a Sensoray Multifunction analog/digital I/O—Model 826 data acquisition card (DAQ) to receive the controlling inputs.

FIG. 1 depicts a magnetic field generating system 10 incorporating the above-described field generating apparatus including an array of eight stationary current-controlled electromagnetic coils 12 arranged around a workspace 14, and used to actuate a magnetic needle tip having a colored end (not shown). Two cameras 16, 18 are used to track the colored tip. A work space cube of phantom tissue material (not shown) may be inserted through an access opening and fixed within the workspace 14, which is arranged at a center of the array of electromagnetic coils 12. An aluminum frame 20 is provided to support the cameras 16, 18 and array of electromagnetic coils 12. In use, the electromagnetic coils 12 may be individually controlled to apply magnetic fields to induce movement of a magnetic needle tip within phantom tissue material located within the workspace 14.

In sufficiently soft mediums or in a sufficiently strong magnetic field, a magnetized body (e.g., incorporating a needle of a premagnetized material) becomes aligned with magnetic flux, as the environmental resistance to rotation is small. In such cases, magnetic flux density can be used to define the desired orientation of a needle. Force applied on the needle is determined by the magnetic gradient in each direction and the magnetization of the needle tip. When the magnetic field generating system 10 is used, both magnetic flux and gradient are produced by the linear combination of the contribution of electromagnetic coil 12 to the net magnetic field. These contributions may be determined through a calibration process that characterizes each the magnetic field contribution of each electromagnetic coil 12 in x, y, and z coordinates at a specific power level (e.g., one Ampere). The magnetic flux and force can be defined, and the current through each coil ($i_0 \ldots i_7$) can be calculated as, $$\begin{bmatrix} i_0 \\ \vdots \\ i_7 \end{bmatrix} = \begin{bmatrix} B(P) \\ m^T B_x(P) \\ m^T B_y(P) \\ m^T B_z(P) \end{bmatrix}^{\dagger} \begin{bmatrix} B_{desired} \\ F_{desired} \end{bmatrix}, \quad (1)$$

where B represents the magnetic field contribution of each of the eight electromagnetic coils 12 at a particular position P. $B_x$, $B_y$, $B_z$ are the gradients of the calibration matrix in each direction at the same position P, $B_{desired}$ is the desired flux density in each direction $F_{desired}$ is the desired force in each direction, m is the magnetization vector of the needle tip, and † represents the pseudo-inverse. In the case of the magnetic field generating system 10 used for experiments described herein, the maximum magnetic flux density that can be produced was 32 mT, and the maximum magnetic gradient was 1.4 $Tm^{-1}$. These limitations were provided exist to avoid overheating of the electromagnetic coils, since the current of electromagnetic coil 12 is limited to 12 Amperes.

By experimentally showing that the disclosed method can be used to steer a sharp needle tip and elastic shaft in soft phantom tissues, it is fully anticipated that a needle may be steered through much stiffer tissues using a magnetic field and gradient of sufficient strength. Magnetic Resonance Imaging (MRI) machines have been shown capable of actuating small particles in both living and phantom arterial channels. A typical commercial medical MRI machine is 15 to 45 times stronger than the magnetic field generating system 10 described in connection with FIG. 1, with such a MRI machine being capable of producing a magnetic flux density between 0.5 and 1.5 Teslas.

Figure 2:
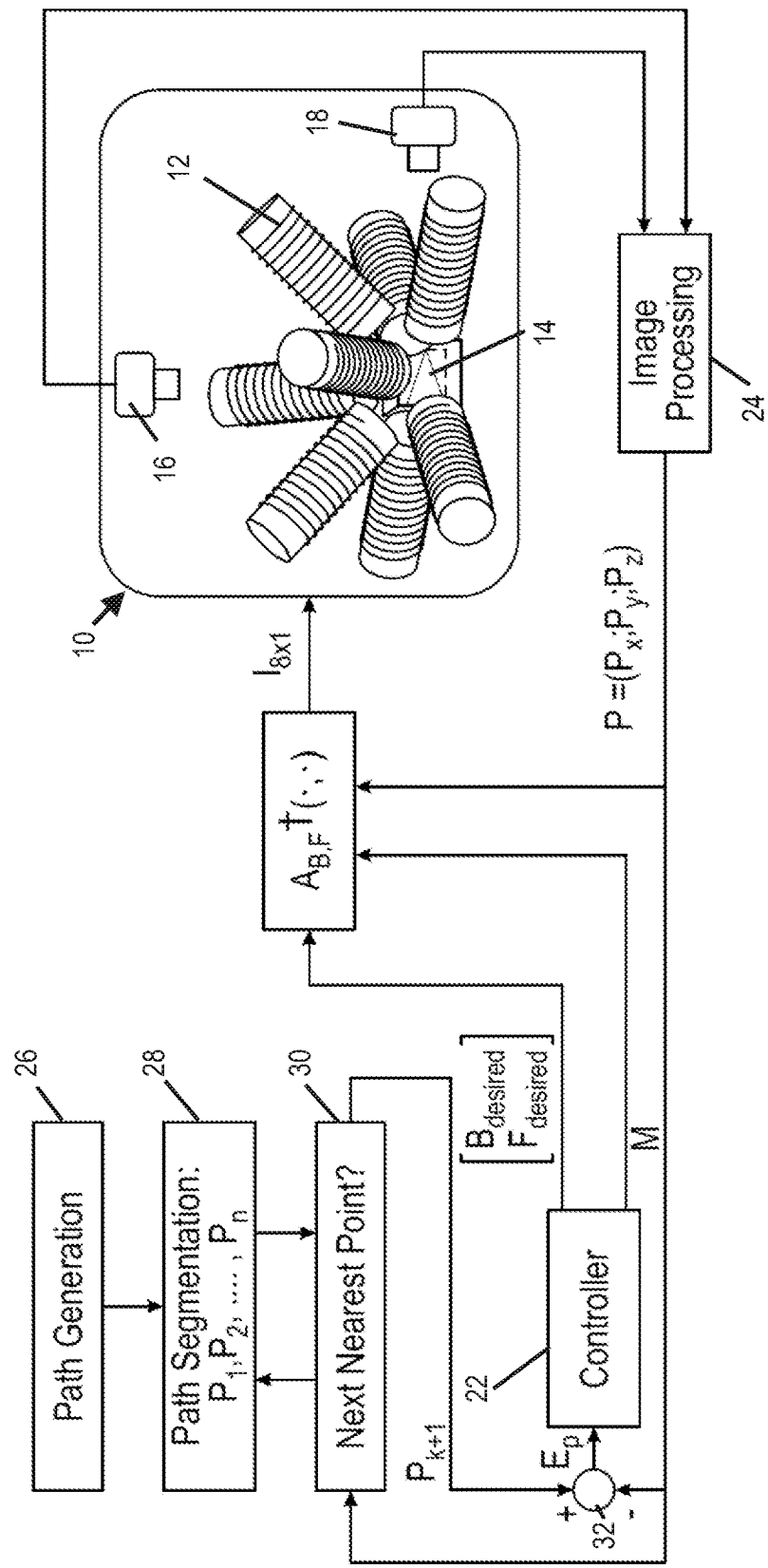
FIG. 2 is a block diagram outlining a control scheme for the magnetic field generating system of FIG. 1 to control movement of a magnetic needle tip.

FIG. 2 is a block diagram outlining a control scheme for the magnetic field generating system 10 of FIG. 1 to control movement of a magnetic needle tip. As shown, the magnetic field generating system 10 includes eight electromagnetic coils 12 and two cameras 16, 18 arranged around a workspace 14 centrally located between the electromagnetic coils 12. The cameras 16, 18 are coupled to an imaging processing apparatus 24. Functional blocks include path generation 26, path segmentation 28 (by which path segments $P_1$ to $P_n$ are defined), and comparison of path segments to the next nearest point 30. An output signal of the image processing apparatus 24 may be provided to the next nearest point block 30, with an output signal thereof being supplied through a comparator 32 to a controller 22 that is configured to supply control signals for control of current supplied to the eight individual electromagnetic coils 12.

Phantom Tissue Selection and Fabrication

Two phantom tissue materials were selected carefully, considering the strength of the magnetic field generating system 10 described in connection with FIG. 1, and the requirement of transparency for the coil system's color-detection-based object tracking software. Two phantom tissues were used to simulate the needle passing through one tissue into another, and to test the ability of the system to achieve a consistent radius of curvature of the needle in different tissues. The two tissue materials chosen are referred to hereinafter as "soft tissue" and "stiff tissue".

The soft tissue was fabricated from a mixture of 0.12 grams per mL of agar gelling powder and 0.08 grams per mL of pure agarose powder. The stiff tissue was fabricated from a mixture of 0.16 grams per mL of gelling agar powder and 35 mcg per mL of pure charcoal. The soft tissue was characterized by a much greater capacity for elastic deformation before rupture; contrasting with the stiff tissue, which ruptured before significant deformations were observed. This mechanical difference is obvious in the results obtained in the following experiments. The agar gelling powder is produced by Nitta-Gelatin, and is composed of 11% locust bean gum, 9% carrageenan, 3% phosphorus acid, and 77% glucose. The agarose powder is molecular biology grade Agarose LE powder from Benchmark Scientific. The pure charcoal powder is produced by General's. Weights are measured using a US Solid Digital Analytical Balance USS-DB55 balance. Both soft and hard phantom tissues were used in the characterization experiments, radius of curvature experiments, and tissue-tissue interface experiments. These materials were chosen for their relatively quick set time and transparency. The concentrations of the soft and stiff phantom tissues were determined through several iterations of experiments during preliminary exercises exploring the capabilities of the coil system.

Needle Selection and Fabrication

For experimentation, it was necessary to develop a needle that embodies two key characteristics that affect the amount of force required to move it through the phantom tissues. Firstly, the needle must be sufficiently magnetized to allow for enough force to be generated by the coil system, and secondly, the needle must have a sharp tip to further reduce required forces. For needles tested according to the experimental methods described herein, a very small permanent magnet acted as the magnetic element, and a needle tip adhered to the magnet with a cyanoacrylate adhesive acted as the sharp element. The magnet was painted red and blue with a dibutyl phthalate/toluene/formaldehyde resin paint so that the tip and rear of the needle can be detected and differentiated via color detection software. The colorant and adhesive were chosen to be inert with respect to the phantom tissue material.

The magnets were chosen based on size, magnetic grade, coating material, and weight. The chosen magnet had dimensions of 3.2 mm by 1.6 mm by 1.6 mm. The magnet was grade N42, was nickel coated, weighed 0.060 g, and had a residual flux density of 1.32 Teslas. From the dimensions and residual flux density, the magnet was calculated to provide a surface field of 0.6353 Teslas. Rectangular magnets were chosen instead of cylindrical magnets because of availability at the required size and grade.

Ten needle tips 50A-50J each including a needle portion 55A-55J and a magnet portion 52A-52J as shown in FIGS. 3A-3J, were selected and fabricated for characterization. Seven needle portions 55A-55G were selected to be cut from various medical needle tips, with the remaining three needle portions 50H-50J being selected from standardized diamond-shaped needles. The first seven needle portions 55A-55G were cut using a diamond dusted cutting disc on a hand-held dremel tool and a 3D printed holder, to be 4 mm with a tolerance of ±10%. Each needle portion 55A-55J was attached to a corresponding magnet portion 52A-52J to yield a needle tip 50A-50J having a length of 7.2 mm, with each needle tip 50A-50J having a pointed end 51A-51J. Each magnet portion 52A-52J included a medial portion 53A-53J painted red, and a distal portion 54A-54J painted blue. FIG. 3A depicts a needle tip 50A (referred to as 88N in FIGS. 6A-6B) including a 0.88 mm diamond shaped needle portion 55A. FIG. 3B depicts a needle tip 50B (referred to as 12N in FIGS. 6A-6B) including a 1.2 mm diamond shaped needle portion 55B. FIG. 3C depicts a needle tip 50C (referred to as 16N in FIGS. 6A-6B) including a 1.6 mm diamond shaped needle portion 55C. FIG. 3D depicts a needle tip 50D (referred to as 14G in FIGS. 6A-6B) including a fourteen gauge medical needle serving as the needle portion 55D. FIG. 3E depicts a needle tip 50E (referred to as 16G in FIGS. 6A-6B) including a sixteen gauge medical needle serving as the needle portion 55E. FIG. 3F depicts a needle tip 50F (referred to as 18G in FIGS. 6A-6B) including an eighteen gauge medical needle serving as the needle portion 55F. FIG. 3G depicts a needle tip 50G (referred to as 19G in FIGS. 6A-6B) including a nineteen gauge medical needle serving as the needle portion 55G. FIG. 3H depicts a needle tip 50H (referred to as 20G in FIGS. 6A-6B) including a twenty gauge medical needle serving as the needle portion 55H. FIG. 3I depicts a needle tip 50I (referred to as 25G in FIGS. 6A-6B) including a twenty-five gauge medical needle serving as the needle portion 55I. FIG. 3J depicts a needle tip 50J (referred to as 30G in FIGS. 6A-6B) including a thirty gauge medical needle serving as the needle portion 55J.

Figure 4:
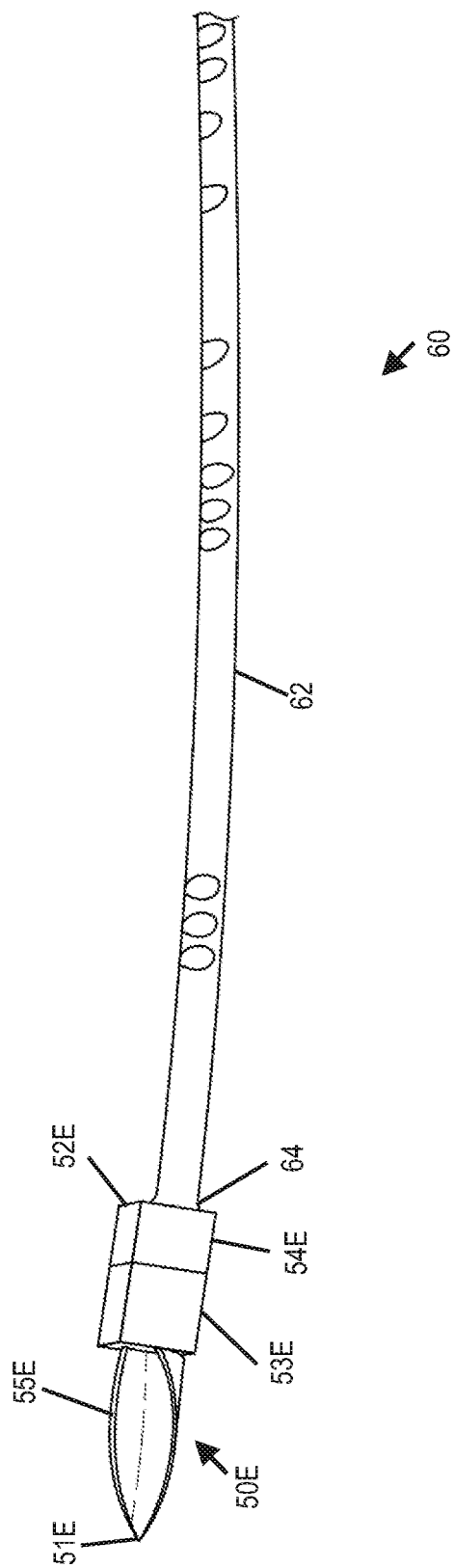
FIG. 4 is a side elevational view of the magnetic needle tip of FIG. 3E coupled to a shaft (i.e., an elongated body structure).

FIG. 4 is a side elevational view of the magnetic needle tip 50E of FIG. 3E coupled to an elongated body structure in the form of a shaft 62 to form a magnetically actuated needle 60.

Figure 5:
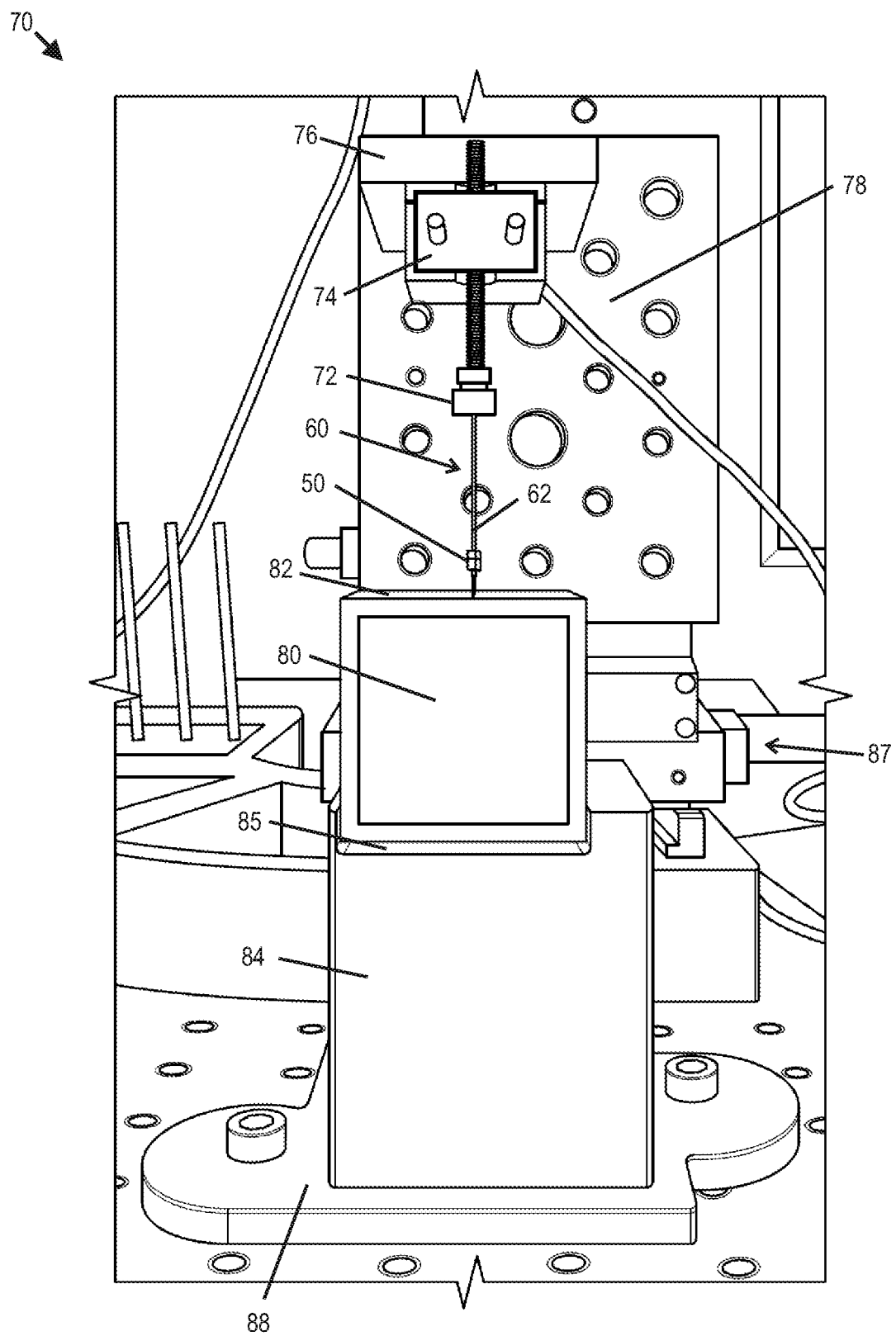
FIG. 5 is a side elevational view illustration of an experimental setup including a translation stage, load cell, and associated equipment for inserting a magnetic needle into phantom tissue to perform needle characterization experiments.

The needle tips 50A-50J of FIGS. 3A-3J were each affixed to a shaft (e.g., according to the shaft 62 shown in FIG. 4) and tested to characterize the force profile of puncture and insertion of the needle tip into phantom tissue, insertion of the magnet into the phantom tissue, and movement through the phantom tissue. These characterization experiments were performed with an experimental setup 70 providing force measurement capability as shown in FIG. 5. The experimental setup 70 included a motorized stage 78 (i.e., a Thorlabs model MT1-Z825V actuated 3-axis stage) configured to effectuate movement of a needle holder 72 supporting a magnetically actuated needle 60 (i.e., including a magnetic needle tip 50 and a shaft 62). The needle holder 72 was affixed to a load cell 74 (i.e., Transducer Techniques model GSO-50 load cell) suspended by an upper support 76 affixed to the motorized stage 78. Phantom tissue 80 was arranged below the load cell 74 to receive the magnetically actuated needle 60, with the phantom tissue 80 being supported within the recess 85 of a sample holder 84 arranged on a base. Vibration reduction was provided by a vibration control table 88 (i.e., Newport Integrity 3), and both a motor controller (i.e., Thorlabs TDC001 motor control) and an Interface USB-enabled data acquisition unit (a Windows personal computer running a LabVIEW program) were provided. The translational stage 78 was programmed to translate such that the magnetic needle tip 50 punctured through a top surface 82 of the phantom tissue 80 and moved through the phantom tissue 80 for some additional distance, totaling a translation of 25 mm. Force was measured throughout the entire process, namely, during needle tip puncture and insertion, magnet insertion, and movement within the interior of the phantom tissue.

The two experimental variables for this experiment were the needle tip design and the phantom tissue material. Ten needle tips and two phantom tissue materials were used. The velocity of each needle was kept constant at 0.5 mm per second. The experimental process consisted of the following steps: first, the needle assembly 60 was set into the needle holder 72, and hot-glue was applied for added restriction; second, the needle holder 72 was attached to the load cell 74 and the load cell 74 was zeroed; third, measurement was initiated, with the downward velocity of the motorized stage 78 set to 0.5 mm per second via the LabVIEW control program; and finally, when the translation stage 78 moved 25 mm, the experiment was complete. After completing all experiments with a particular needle, the hot glue was removed chemically with 99% isopropyl alcohol to allow the next needle to take its place.

Soft Tissue-Stiff Tissue Interface

In conventional methods of needle steering utilizing a rotating base and beveled needle, one issue that is encountered is the deflection of the needle tip as a result of passing through a tissue membrane. At low approach angles, a conventional needle tip deflects along the interface boundary and continues along an unplanned trajectory. Noting this limitation, an experiment was developed to determine the behavior of the magnetic needle steering method of the present disclosure regarding passage through a similar barrier. In these experiments, a magnetic needle tip was forced to pass through an interface plane of two different phantom tissues at three different angles of attack. Each needle was steered via a closed loop controller receiving visual feedback from two cameras and controlling the current through each coil. The position of the needle was measured over the course of the experiment. Six experimental cases were designed: three angles of attack (90 degrees, 45 degrees, and 22.5 degrees), for two transition types (soft-to-stiff and stiff-to-soft tissue transitions). The first through third cases covered soft tissue to stiff tissue transitions, and the fourth through sixth cases covered stiff tissue to soft tissue transitions. The angle of attack (AoA) in cases one and four was 90 degrees; in cases two and six the AoA was 45 degrees; and in cases three and five the AoA was 22.5 degrees. A magnetic field generating system generated a magnetic field that aligned the needle to the specified angle for the particular experimental case and simultaneously generated a pulsing magnetic field gradient to apply force to the needle in the same direction. A proportional-integral-derivative (PID) controller was employed to manipulate the magnitude of the force pulses. The program was stopped manually after the needle sufficiently crossed the planar interface between two different phantom tissues.

The experimental system utilized three PID controllers in the execution of the path-following program, with one PID controller for each positional degree of freedom (x, y, z). Needle orientation was assumed to be in line with the magnetic field. This is a good assumption in delicate tissues, and the addition of three controllers to correct orientation would null this assumption in the case of more rigid tissues. Notably, system performance may be improved by further tuning the controllers used by the system Radius of Curvature Experiment In conventional needle steering methods, a limiting factor is the minimum radius of curvature that is achievable by the needle system. The radius of curvature in conventional needle steering methods is constant and depends on the characteristics of the particular needle and tissue pair interactions. The result is that for any given tissue/needle combination, only one radius of curvature is attainable without the use of complex mechanisms such as manipulating the tissue via external forces or duty-cycling the rotation of the needle. One benefit of the magnetically driven system according to the present disclosure is that the radius of curvature is arbitrary. The inventors sought to determine whether this arbitrary variability allows for superior turning radii compared to conventional needle steering methods. To test this, an experiment was designed and executed to showcase the variability and advanced dexterity achievable by the magnetic steering method. This experiment demonstrated the ability of the system to achieve arbitrary radii of curvature down to 10.16 mm in both the "soft" and "stiff" phantom tissues. The experiment consisted of the needle tip following three different predetermined circular paths through two different phantom tissue materials, under closed-loop position feedback control. Three radii of curvature were chosen (10.16 mm, 20.32 mm, and 30.48 mm), and each radius was tested in both soft and stiff phantom tissues. A circular path with respect to the current position of each needle tip was generated. The system then used visual feedback in conjunction with three PID controllers, relating the error between the current position and the position of the next path point in x, y, and z directions to desired force in the respective direction. This system sequentially aligned position of a needle tip to each point along a generated path. The needle orientation was assumed to be in-line with the applied magnetic aligning field, which is an accurate assumption given a sufficiently powerful magnetic field.

Needle Characterization

To evaluate different needle tips when puncturing and moving through the phantom tissues, the force profiles of each needle tip in each phantom tissue was compared. Three regions of interest in the needle insertion force profiles were characterized individually for each needle/tissue pair in FIGS. 6A and 6B. These regions correspond to two peaks that occur during the puncturing process, and the steady state force that is observed when moving through the tissue. The first peak coincides with the initial puncture of the needle tip into the phantom tissue surface, labeled "needle tip insertion" peak. Sharper needles experience smaller force values in this region. The second peak observed coincides with the insertion of the magnet body into the phantom tissue. Needle tips having a smaller diameter have a larger exposed magnet face, and thus experience greater force during this second peak, the "magnet insertion" peak. The third region is the internal movement force; the force required to move through the tissue while the entire body is inside during a steady state, labeled the "SS internal movement" region.

The initial puncture force ranged from about 2 mN to about 18 mN in the soft tissue, and from about 1 mN to 6 mN in the stiff tissue. The force required for the insertion of the magnet ranges from 3 mN to about 12 mN in the soft tissue, and from 2 mN to about 18 mN in the stiff tissue. The forces required for internal movement through the phantom tissues ranged from 0.6 mN to 1.3 mN for the soft tissue and 1.4 mN to 2.6 mN for the stiff tissue.

Figure 6A:
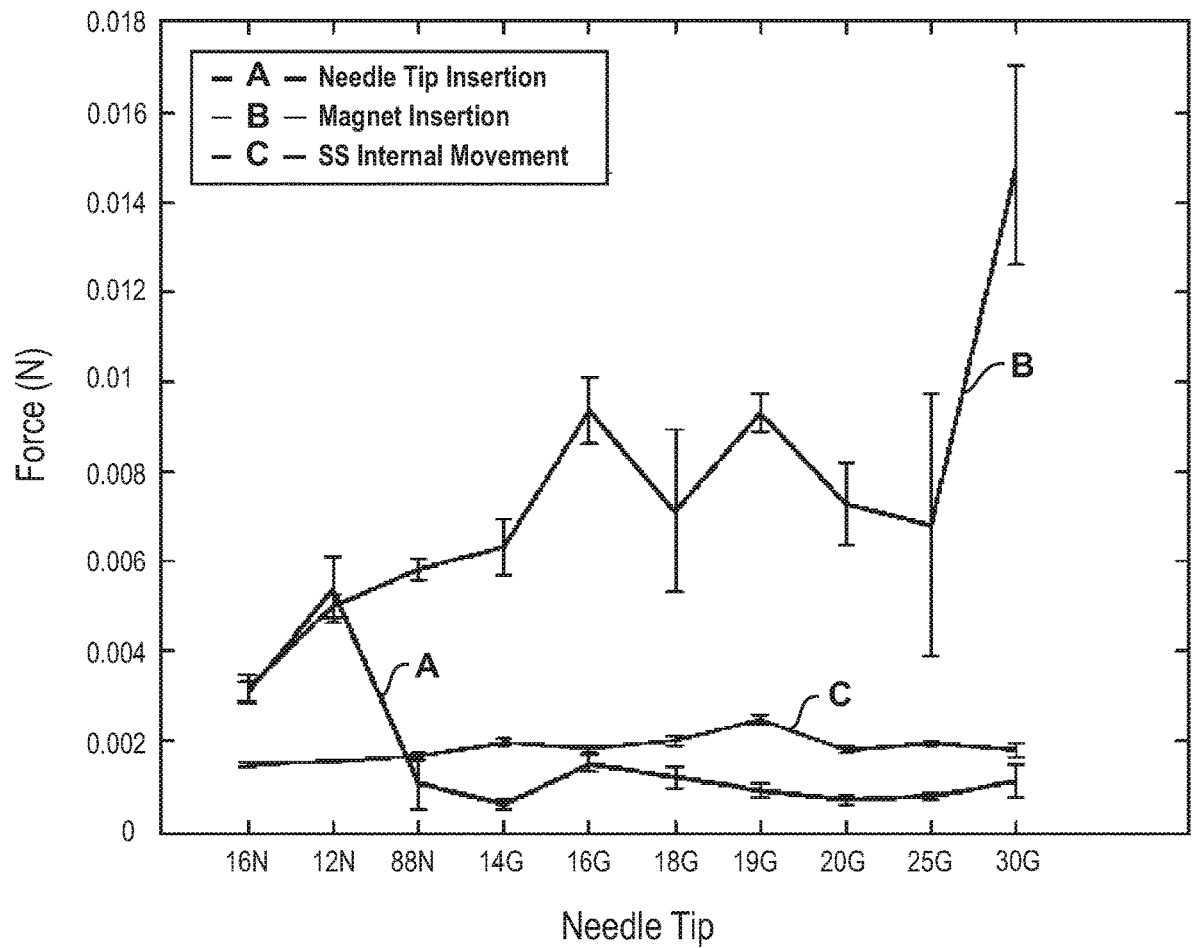
FIG. 6A is a plot of force versus needle tip for insertion of ten needle tips into stiff phantom tissue.
Figure 6B:
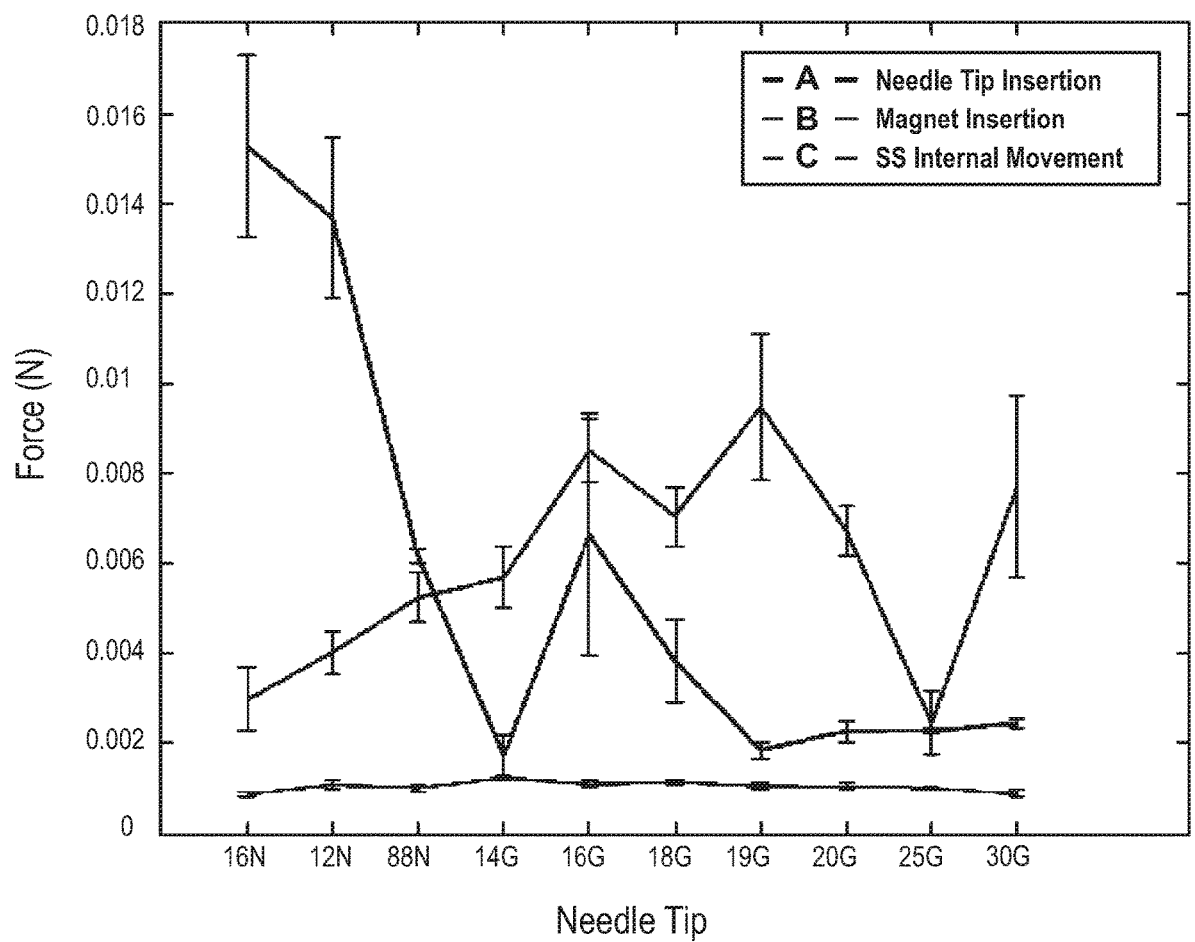
FIG. 6B is a plot of force versus needle tip for insertion of ten needle tips into soft phantom tissue.

FIGS. 6A and 6B compare the performance of each needle, with FIG. 6A plotting force values for needles characterized in stiff tissue, and FIG. 6B plotting force values for needles characterized in soft tissue. The maximum force for each needle observed at each of the three aforementioned regions is shown.

The fact that the 1.6 mm diamond-point tipped needle ("16N") had relatively small magnet insertion force in both the soft and stiff phantom tissues makes sense, as this needle design exhibited the least amount of exposed magnet surface. Interestingly, this needle tip also proved to have the best internal movement force profile over all experiments, requiring the least internal movement force in the soft tissue and the second least internal movement force in the stiff tissue. This needle was selected as optimal among the tips tested to achieve the test criteria.

This needle tip was not meant to be the best design for use in surgical applications, but was chosen to demonstrate the disclosed needle steering method in the phantom tissue. Additional research on magnetic needle tip design may yield configurations better suited achieving minimal force profiles in future (e.g., surgical) applications.

Tissue-Tissue Interface

Figure 7B:
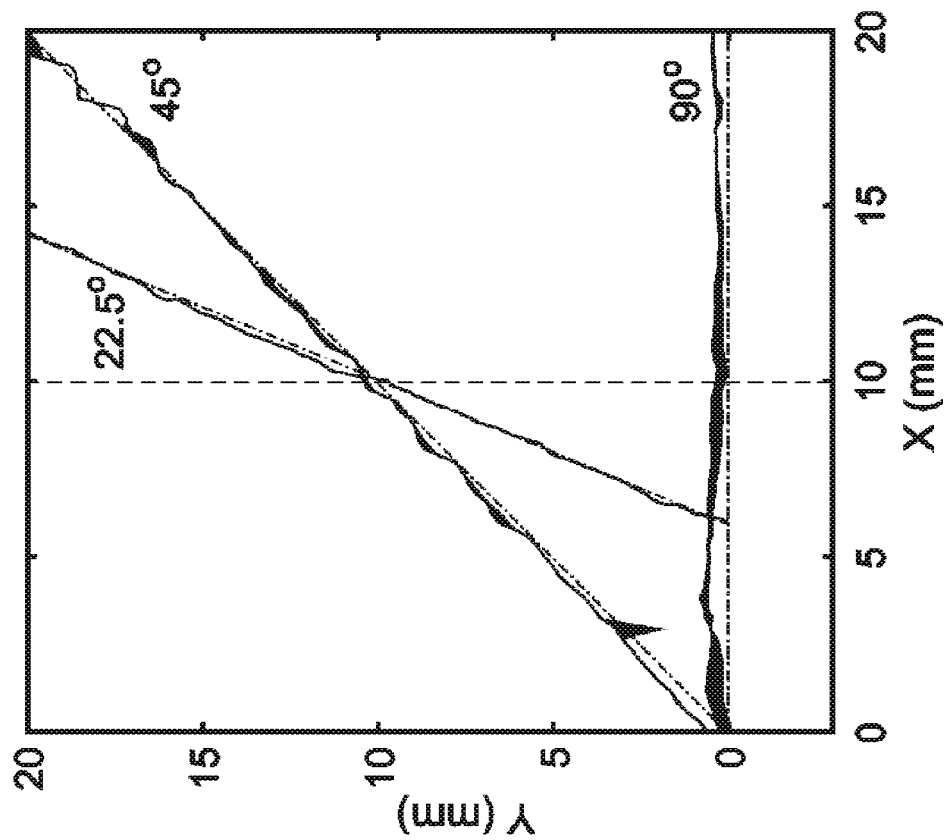
FIG. 7B is a plot of actual paths (in x, y coordinates) followed by needle tips for multiple experimental cases at three inclination angles for passage of needles through a soft to stiff phantom tissue transition.
Figure 7A:
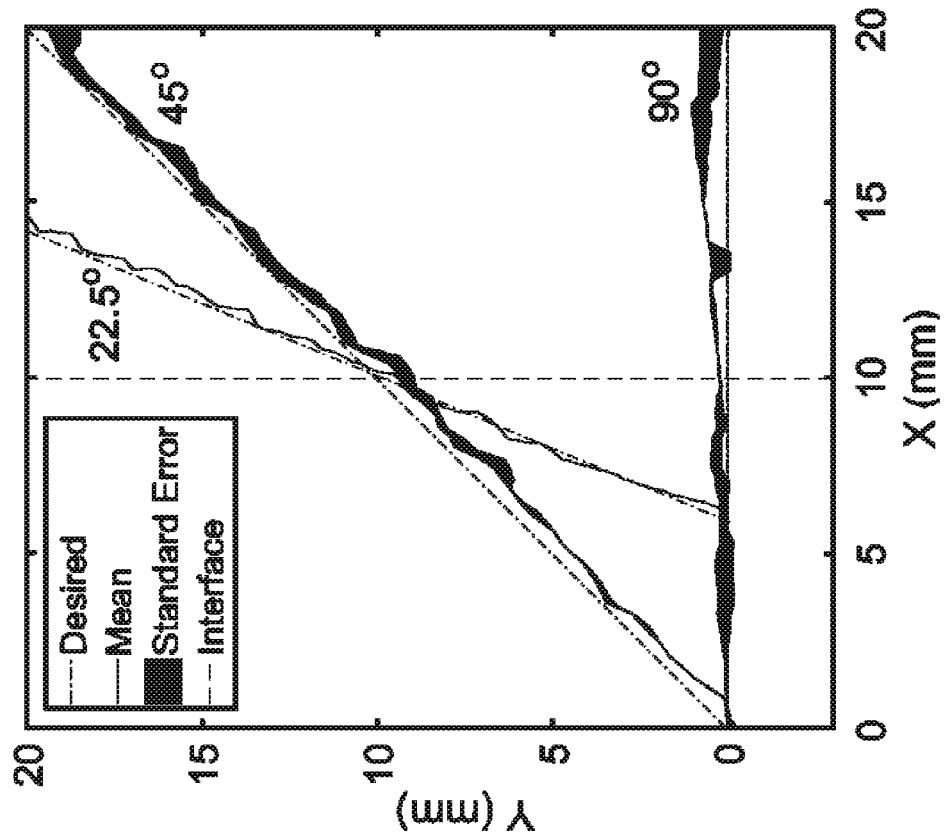
FIG. 7A is a plot of actual paths (in x, y coordinates) followed by needle tips for multiple experimental cases at three inclination angles for passage of needles through a stiff to soft phantom tissue transition.

FIG. 7A is a plot of actual paths (in x, y coordinates) followed by needle tips for multiple experimental cases at three inclination angles for passage of needles through a stiff to soft phantom tissue transition. FIG. 7B is a plot of actual paths (in x, y coordinates) followed by needle tips for multiple experimental cases at three inclination angles for passage of needles through a soft to stiff phantom tissue transition.

FIG. 9 is a table summarizing experimental cases and the associated deviation of the experimental mean from the ideal path for passage of magnetic needle tips through interfaces between phantom tissues of different stiffnesses according to the paths characterized in FIGS. 7A-7B. The ideal path is defined as a line following the defined AoA from the needle's starting position. Transition type describes the starting and ending tissue types for the experiment. Desired AoA is the angle along which forces are applied to motivate the magnetic needle tip to move.

The needle tip chosen for use in experiments had a diameter of 1.59 mm. All deviations of experimental means from the desired paths are less than 2.3 mm with the overall RMS error of 1.2 mm, demonstrating the ability of the method to greatly improve upon the issue of tissue boundary deflection. In addition, these interface experiments showcase the ability of the proposed method to maintain a straight path through a uniform medium as well as an interface of tissues with different stiffness. Needles according to the present disclosure perform better in the stiff tissue than soft tissue, achieving maximum deviations of under 1 mm in certain instances.

In conventional needle steering methods, the needle tip experiences significant deflection after it crosses a simulated membrane during insertion at shallow angles of attack. For example, a tip deviation of over 1 cm has been reported between the final tip position of an insertion through a simulated membrane and a control insertion. In the interface experiments presented in this disclosure, however, the needle is able to correct its trajectory and follow the desired path after puncturing a tissue interface. Notably, providing an advanced ability to achieve much smaller radii of curvature during insertion may entirely eliminate many situations in which extremely sharp angles of attack are unavoidable.

Radius of Curvature

In order to demonstrate the performance of the disclosed needle steering technique in making sharp turns, three different radii of curvature were tested: 10.2 mm, 20.3 mm, and 30.5 mm in both soft and stiff phantom tissues.

Figure 8B:
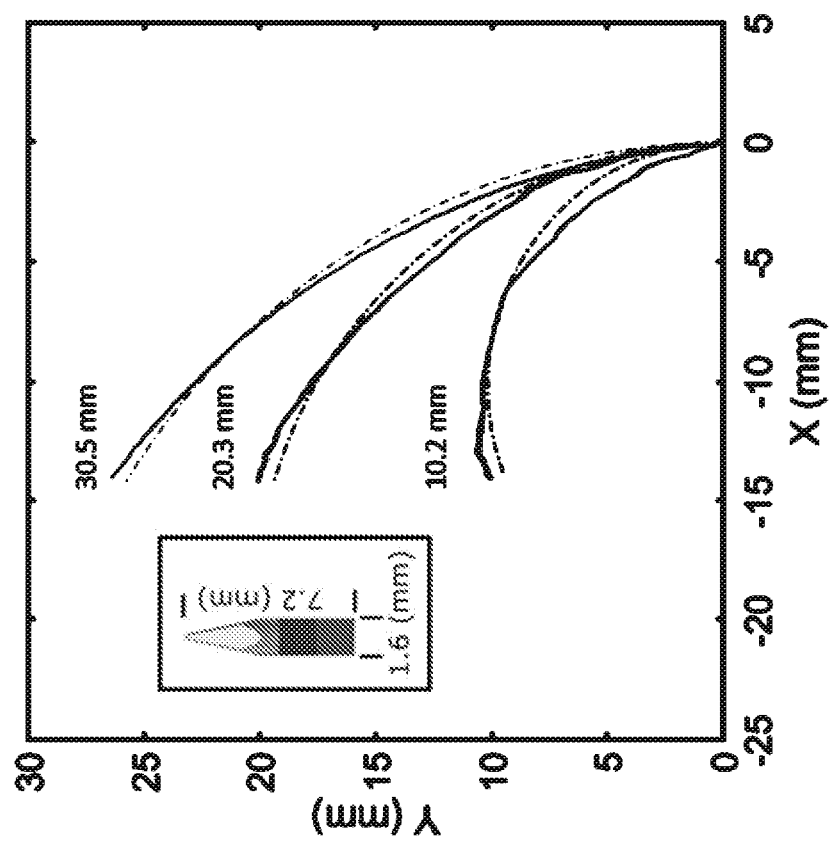
FIG. 8B is a plot of position (in x, y coordinates) of a magnetic needle tip following circular paths through three different radii of curvature in soft phantom tissue.
Figure 8A:
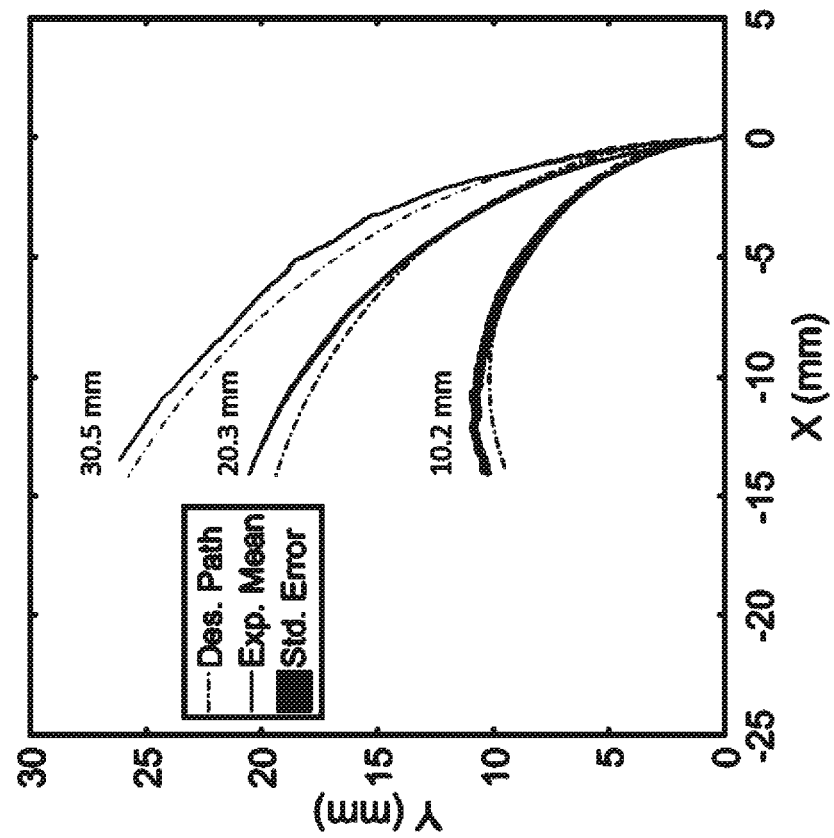
FIG. 8A is a plot of position (in x, y coordinates) of a magnetic needle tip following circular paths through three different radii of curvature in stiff phantom tissue.

FIG. 8A is a plot of position (in x, y coordinates) of a magnetic needle tip following circular paths through three different radii of curvature in stiff phantom tissue. FIG. 8B is a plot of position (in x, y coordinates) of a magnetic needle tip following circular paths through three different radii of curvature in soft phantom tissue.

Complex Trajectory

FIG. 10 is a table summarizing experimental cases and the associated maximum deviation of the experimental mean from the ideal path for passage of magnetic needle tips along circular paths through three different radii of curvature in soft and stiff phantom tissues as characterized in FIGS. 8A-8B.

The needle performs better in the soft phantom tissue than stiff, achieving maximum deviations of 0.8 mm and RMS error of 1.3 mm or less. Overall, for the chosen experimental needle tip having a diameter of 1.59 mm, the predefined curved paths are achieved with maximum deviations under 1.5 mm. The RMS error for all of the radius of curvature experiments is also 1.4 mm.

A minimal, repeatable, reliable radius of curvature achieved by a magnetic needle steering method according to the present disclosure is 10.26 mm. This limit is due to the radius of curvature approaching the total length of the needle. As the needle tip length (7.2 mm) and radius of curvature converge, the needle tends to "cut" the tissue with the shaft during rotation around the curve, instead of piercing the tissue with the point during forward motion as intended. Such behavior causes excessive damage to the tissue, and is thus not desirable for needle steering. Smaller radii of curvature would be possible with a shorter needle, but a similar limit will be reached as the curvature approaches the needle tip length.

Figure 11A:
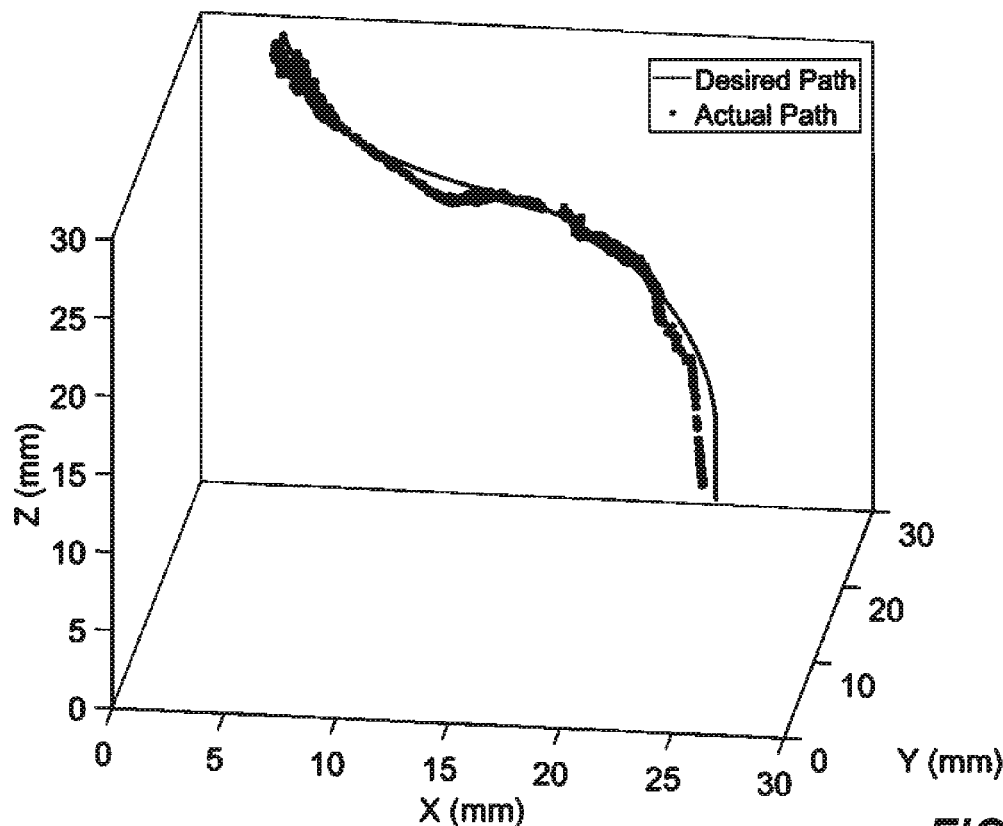
FIG. 11A is a plot of (x, y, z) position of a magnetic needle tip as it followed a defined complex path in stiff phantom tissue.
Figure 11B:
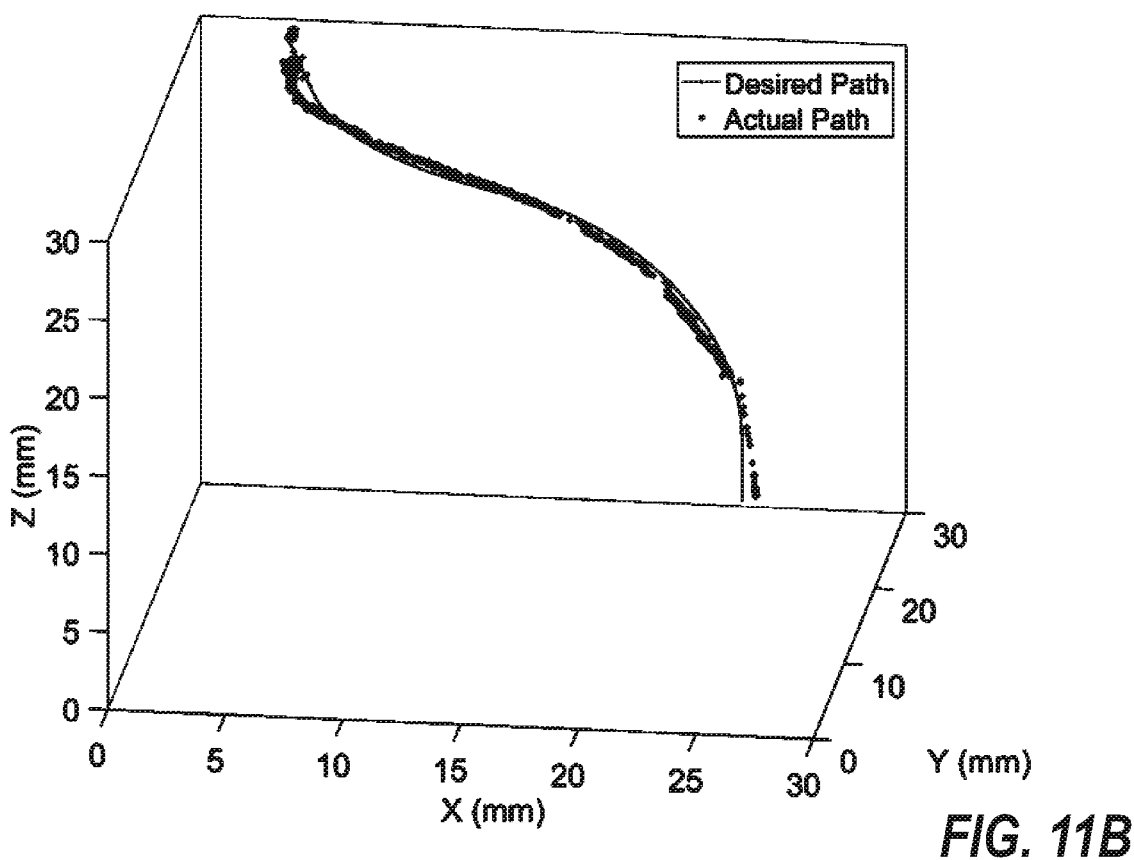
FIG. 11B is a plot of (x, y, z) position of a magnetic needle tip as it followed a defined complex path in soft phantom tissue.

Although FIG. 10 shows the ability of embodiments disclosed herein to take variable radii of curvature in a 2D plane, it is necessary to be able to maneuver in all three dimensions (3D) for clinical applications. Systems and methods disclosed herein are capable of generating a magnetic field in any direction, which makes it possible for a magnetic needle to travel on any path. This also enables any radius of curvature between the minimum possible radius and the straight line to be taken in 3D, as demonstrated by the experiments in this section. Complex 3D path experiments were performed. The results of these complex 3D path experiments are shown in FIGS. 11A-11B. FIG. 11A is a plot of (x, y, z) position of a magnetic needle tip as it followed a defined complex path in stiff phantom tissue. FIG. 11B is a plot of (x, y, z) position of a magnetic needle tip as it followed a defined complex path in soft phantom tissue.

As shown in FIGS. 11A-11B, a 1.59 mm diameter needle is able to accurately follow the predefined path with a maximum error of 2.4 mm in the soft gel, and 2.7 mm in the stiff gel. The RMS error in the soft and stiff gels is also 0.9 mm and 0.4 mm, respectively. As shown by these experiments, this proposed method allows for steering the needle through mediums on complex 3D paths without causing any of the excess tissue damage that would be caused by conventional needle steering methods Demonstrating that the disclosed method is capable of steering a sharp needle tip and elastic shaft in relatively soft phantom tissues, it can be reasonably predicted that a needle can be steered through much stiffer tissues using a magnetic field and gradient of sufficient strength. Magnetic Resonance Imaging (MRI) machines have been shown to be capable of actuating small particles in both living and phantom arterial channels. A typical commercial medical MRI is 15 to 45 times stronger than the coil system used in this research, being capable of producing a magnetic flux density between 0.5 and 1.5 Teslas. "High field" and "ultra-high field" MRI machines are capable of producing magnetic fields from 3.0 Teslas to 10 Teslas, and at the time of writing, MRI and MRS systems capable of producing fields over 20 Teslas are in existence. Thus, a commercial MRI system or other magnetic coil systems having sufficient strength can be used to steer magnetic needles and perform surgical procedures in stiffer tissues.

By presenting a new method of needle steering, several drawbacks of the current needle steering techniques have been eliminated and various improvements to the state of the art have been demonstrated. Compression and torsion effects, such as buckling of the needle shaft, are significant draw-backs to the traditional needle steering methods that cause unnecessary damage in tissue, inaccuracies in control, and increased model complexity. These drawbacks are done away with in the magnetic needle steering method by design, as the elastic shaft is not load bearing in compression or torsion. In addition, the disclosed method does not suffer from significant deflections when crossing a tissue boundary, and can reliably move along a predetermined linear path through two different tissues and the interface boundary between them. The consistent performance of arbitrary radius of curvature in different materials is very significant, as the human body consists of many different tissue materials and interfaces. Moreover, repeatable path following at arbitrary radii of curvature down to 10.16 mm is shown possible in different tissue materials, compared to 15.5 mm as the minimal reported radius of curvature achieved by the traditional needle steering method, and 31 mm as a more realistic minimum radius achieved by other researchers (e.g., Wedlick and Okamura). Finally, the disclosed magnetic needle steering method is also promising for its potential ease of development for clinical applications, as the technology for human scale medical electromagnets is well established.

Compression and torsion effects, like buckling and torsional spring/damper characteristics of the needle shaft, are significant drawbacks to the traditional needle steering method, potentially causing unnecessary damage in tissue, inaccuracies in control, and increased model complexity. These stress effects are eliminated with the magnetic needle steering method by design, as the elastic shaft is not compressively or torsionally load bearing. Methods disclosed herein do not suffer from significant deflections when crossing a tissue boundary, and can reliably move along a predefined through two different tissues and the interface boundary between them.

The magnetic needle steering method presented is also promising for its potential ease of large scale execution, as many hospitals are already equipped with a commercial MRI machine. Commercial MRI machines have already been shown capable of magnetically steering magnetic particles, proving that these machines are capable of being purposed towards the controlled actuation of magnetic particles in a living body.

Embodiments disclosed herein may be applied to numerous end uses, generally including administering or drawing fluids to or from the body. Specific end uses including treatment of deeply embedded cancerous tumors (e.g., in the brain) via compartmental therapy such as (but not limited to) Convection-Enhanced delivery (a targeted drug delivery technique for the brain utilizing a pressure gradient to deliver pharmaceutical agents across the blood-brain barrier). Another application that would benefit from tight needle steering is radiofrequency ablation (RFA) of tumors (e.g., liver tumors). In RFA, a tumor or other target tissue is thermally destroyed by heat induced by high frequency alternating current, applied at the end effector of a small electrode.

Those skilled in the art will recognize improvements and modifications to the preferred embodiments of the present disclosure. All such improvements and modifications are considered within the scope of the concepts disclosed herein and the claims that follow. Any of the various features and elements as disclosed herein may be combined with one or more other disclosed features and elements unless indicated to the contrary herein.

The invention claimed is:

1. A system comprising:
a magnetic resonance imaging system that comprises at least one magnetic field source; and
a steerable assembly that comprises an elongated body structure, an implement arranged at a distal end of the elongated body structure, and a premagnetized material arranged closer to the distal end than to a proximal end of the elongated body structure;
wherein the at least one magnetic field source is configured to interact with the premagnetized material to effect movement of the implement within an animal body when the implement is arranged within the animal body.

2. The system of claim 1, wherein at least a portion of the implement comprises the premagnetized material.

3. The system of claim 1, wherein the implement comprises a needle or a surgical tool.

4. The system of claim 1, wherein the implement comprises at least one of a camera or an optical fiber.

5. The system of claim 1, wherein the elongated body structure comprises a hollow tube or a catheter.

6. The system of claim 1, wherein the elongated body structure comprises an electrical conductor or an optical fiber.

7. The system of claim 1, wherein a center of mass of the premagnetized material is located less than 5 cm from the distal end of the elongated body structure.

8. A method for guiding passage of an implement through or within tissue of an animal body, the method comprising:
inserting at least a portion of a steerable assembly into the animal body, the steerable assembly comprising an elongated body structure, an implement arranged at a distal end of the elongated body structure, and a premagnetized material or an electromagnet arranged closer to the distal end than to a proximal end of the elongated body structure;
providing a magnetic resonance imaging system comprising at least one magnetic field source external to an animal body; and
altering at least one of strength or position of the at least one magnetic field source to interact with the premagnetized material or the electromagnet to effectuate movement of the implement within the animal body.

9. The method of claim 8, wherein the elongated body structure comprises a fluidic passage, and the method comprises delivering a therapeutic agent through the fluidic passage and the implement to the tissue.

10. The method of claim 8, wherein the method further comprises extracting a tissue sample from the animal body using the implement.

11. The method of claim 8, wherein the implement comprises a surgical tool, a camera, or an optical fiber.

* * * * *